United States Patent
Leonard (10) Patent No.: US 6,700,658 B2
(45) Date of Patent: Mar. 2, 2004

(54) METHOD AND APPARATUS FOR CIRCUIT PATTERN INSPECTION

(75) Inventor: Patrick F. Leonard, Ann Arbor, MI (US)

(73) Assignee: Electro Scientific Industries, Inc., Portland, OR (US)

( * ) Notice: Subject to any disclaimer, the term of this patent is extended or adjusted under 35 U.S.C. 154(b) by 201 days.

(21) Appl. No.: 09/971,847

(22) Filed: Oct. 5, 2001

(65) Prior Publication Data

US 2003/0067596 A1 Apr. 10, 2003

(51) Int. Cl.$^7$ ............................................... G01N 21/00
(52) U.S. Cl. .................................................. 356/237.1
(58) Field of Search ..................... 355/69, 71; 356/237, 356/237.1, 399–401; 250/548

(56) References Cited

U.S. PATENT DOCUMENTS

| | | | |
|---|---|---|---|
| 4,152,723 A | 5/1979 | McMahon | 358/106 |
| 4,556,903 A | 12/1985 | Blitchington | 358/106 |
| 4,589,140 A | 5/1986 | Bishop et al. | 382/8 |
| 4,635,289 A | 1/1987 | Doyle et al. | 382/8 |
| 4,649,424 A | 3/1987 | Bishop | 357/84 |
| 4,692,690 A | 9/1987 | Hara | 324/73 |
| 4,700,225 A | 10/1987 | Hara | 358/106 |
| 4,772,125 A | 9/1988 | Yoshimura | 356/237 |
| 4,786,170 A | 11/1988 | Groebler | 356/318 |
| 4,816,686 A * | 3/1989 | Hara et al. | 250/458.1 |
| 4,893,346 A | 1/1990 | Bishop | 382/8 |
| 4,928,313 A | 5/1990 | Leonard et al. | 382/8 |
| 4,962,541 A | 10/1990 | Doi et al. | 382/30 |
| 5,008,743 A | 4/1991 | Katzir | 358/101 |
| 5,046,120 A | 9/1991 | Bishop | 382/54 |
| 5,058,982 A | 10/1991 | Katzir | 385/33 |
| 5,119,434 A | 6/1992 | Bishop et al. | 382/8 |
| 5,153,668 A | 10/1992 | Katzir | 356/237 |
| 5,216,479 A | 6/1993 | Dotan | 356/73 |
| 5,278,012 A | 1/1994 | Yamanaka et al. | 430/30 |
| 5,333,052 A | 7/1994 | Finarov | 356/369 |
| 5,450,201 A | 9/1995 | Katzir | 356/369 |
| 5,495,535 A | 2/1996 | Smilansky et al. | 382/145 |
| 5,532,817 A | 7/1996 | DeVries et al. | 356/318 |
| 5,541,416 A * | 7/1996 | Washizuka | 250/458.1 |
| 5,586,058 A | 12/1996 | Aloni et al. | 364/552 |
| 5,774,572 A | 6/1998 | Caspi | 382/141 |
| 5,774,573 A | 6/1998 | Caspi | 382/141 |
| 5,790,694 A | 8/1998 | Maruo | 382/149 |
| 6,014,209 A | 1/2000 | Bishop | 356/237.5 |
| 6,091,488 A * | 7/2000 | Bishop | 356/237.5 |

* cited by examiner

Primary Examiner—Russell Adams
Assistant Examiner—Michelle Nguyen
(74) Attorney, Agent, or Firm—Young & Basile, PC; Thomas E. Bejin (57) ABSTRACT

The present invention captures images of a circuit chip with a time delay integration or TDI sensor. The circuit chip is on a movable stage which moves at the same rate at which the TDI sensor clocks. A pulsed laser is directed toward the circuit chip and activated in synchronisation with the clock rate of the TDI sensor such that laser is activated when the TDI sensor is imaging the object and the laser is deactivated when the TDI sensor is transferring its charge.

21 Claims, 5 Drawing Sheets

METHOD AND APPARATUS FOR CIRCUIT PATTERN INSPECTION

FIELD OF THE INVENTION

The present invention relates to the use of time delay integration sensors and, in particular, the use of time delay integration sensors for inspecting circuit patterns.

BACKGROUND OF THE INVENTION

Many techniques exist to inspect circuit patterns on integrated circuit chips. One such technique involves the use of fluorescence to inspect such patterns. In particular, when certain types of which circuits are composed of organic and inorganic substances are illuminated with certain wave lengths of light, the organic portions fluoresce while the inorganic portions do not, thereby providing a high contrast image for inspection. However, the fluorescence is such that for an image of the chip to be adequately captured by a sensor, that sensor must be exposed for a minimum period of time. This minimum period of time for exposure can limit the rate at which chips move pass the sensor. To increase throughput while maintaining an acceptable degree of quality in the captured images the prior art has provided for the use of time delay integration (TDI) sensors.

Figure 5:
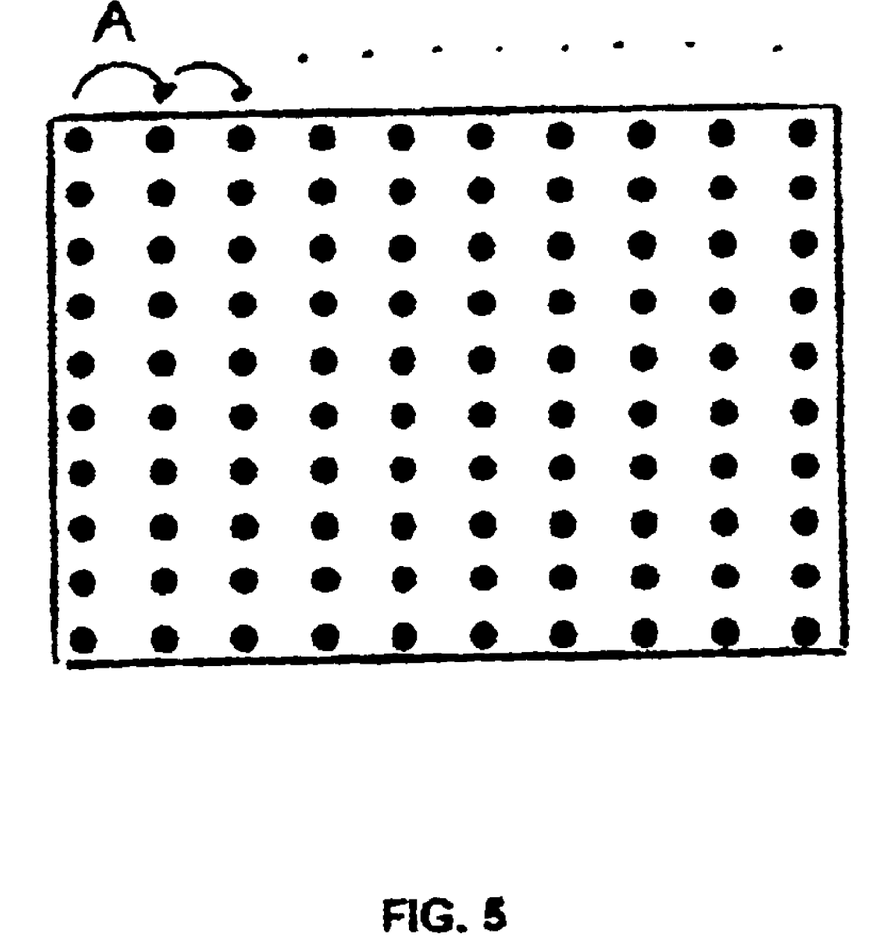
FIG. 5 is a schematic representations illustrating the manner in which a TDI sensor operates.

A typical TDI sensor is generally illustrated in FIG. 5. TDI sensors typically include a two dimensional array of photo sites arranged in rows and columns. At a defined time, the charges in the photo sites of a column are moved, in mass, to the photo sites in the adjacent column as illustrated by arrow A. The rate at which the charges are moved from column to column is called the clock rate. Concurrent with the shifting of the charges in the columns of the TDI sensor, the laser stripe, or circuit chip, moves at the same rate such that the same part of the circuit chip is continuously integrated by subsequent columns of photo sites. By shifting the columns together with the continuous movement of the chip being inspected, prior art systems have increased through put while maintaining acceptable images.

Typical fluorescence inspection systems include a pair of lasers which continuously illuminate the surface. Two lasers are used to eliminate shadows on the circuit chip. Because the lasers are continuous, their power must be decreased to avoid damaging the circuit chip. By de-powering the laser the amount of fluoresce is correspondingly decreased. As described above, the circuit chip is positioned on a stage which moves synchronously with the shifting columns of the TDI sensors. However, there exists a need to improve the quality of images captured in such systems.

SUMMARY OF THE INVENTION

The present invention provides for a circuit chip inspection device and method. In its preferred embodiment the inventive device and method are used for fluorescent inspection of circuit chips.

The circuit chip inspection device is for inspecting a circuit chip where the circuit chip is on a movable stage with the stage moving substantially continuously along an axis at a defined rate. The circuit chip inspection device includes a pulsed laser, a time delay integration (TDI) sensor and a controller. The pulsed laser is operative to emit a stripe of laser pulses at controlled intervals with the pulses being directed toward the circuit chip as to illuminate the circuit chip. The TDI sensor captures an image of the circuit chip. The TDI sensor is defined by an array of photo sites having at least one row of photo sites and a plurality of columns of photo sites. Each photo site is chargeable and the sensor is operative to transfer a charge from column to column at a predefined rate. The TDI sensor and movable stage are coordinated such that the charges are being clocked from column to column at the same rate at which the stage is moving. The controller is connected to the pulsed laser and configured to activate the laser in synchronization with the rate at which the TDI sensor transfers charges from column to column such that the laser is activated when the charge resides in a column and the laser is deactivated when the charge is being transferred from column to column.

Preferably, the controller can be connected to the movable stage and to the TDI sensor; the controller operative in determining whether the stage is moving at the same rate as the rate at which the charges are being shifted from column to column in the TDI sensor with the controller being operative to adjust the rate at which the stage is moving.

The controller can preferably measure the movement of the stage in units of pixels which correspond to the size of the photo sites on the TDI sensor. The controller can then be operative to activate the laser when it determines that the stage has moved a half of a pixel.

The method for inspecting circuit chips according to the present invention is as follows. The circuit chip is on a movable stage with the stage moving substantially continuously along an axis at a defined rate. The method includes imaging the circuit and pulsing a stripe of lasers at the circuit. The circuit is imaged with a time delay integration (TDI) sensor, the TDI sensor defined by an array of photo sites, having at least one row of photo sites and a plurality of columns of photo sites. Each photo site is chargeable and the TDI sensor is operative to transfer a charge from column to column at a predefined rate. The TDI sensor and movable stage are coordinated such that the charges are being clocked from column to column at the same rate at which the stage is moving. The laser stripe is pulsed toward the circuit chip as to illuminate the circuit chip where the laser pulses are in synchronization with the rate at which the sensor transfers charges from column to column such that the laser is activated when the charge resides in a column and the laser is deactivated when the charge is being transferred from column to column.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION OF THE PREFERRED EMBODIMENT

The present invention utilizes a pulsed laser directing pulses of laser stripes at a circuit chip from above. Because the laser pulses are directed from above shadows are eliminated. Preferably the laser is directed toward the chip with a dichroic mirror such that the laser light is reflected but the fluorescent illumination is passed through the dichroic mirror. In this manner a TDI sensor can be positioned directly above the circuit. The laser pulses occur only when a charge resides in a column of the TDI sensor and does not pulse when the charges in the TDI sensors are shifted from column to column. By pulsing the laser in this fashion, the amount of energy delivered to the circuit chip by the laser per TDI integration is increased and by not firing the laser when charges are transferred from one column of photo sites to another artifacts and smearing is significantly reduced.

Figure 1:
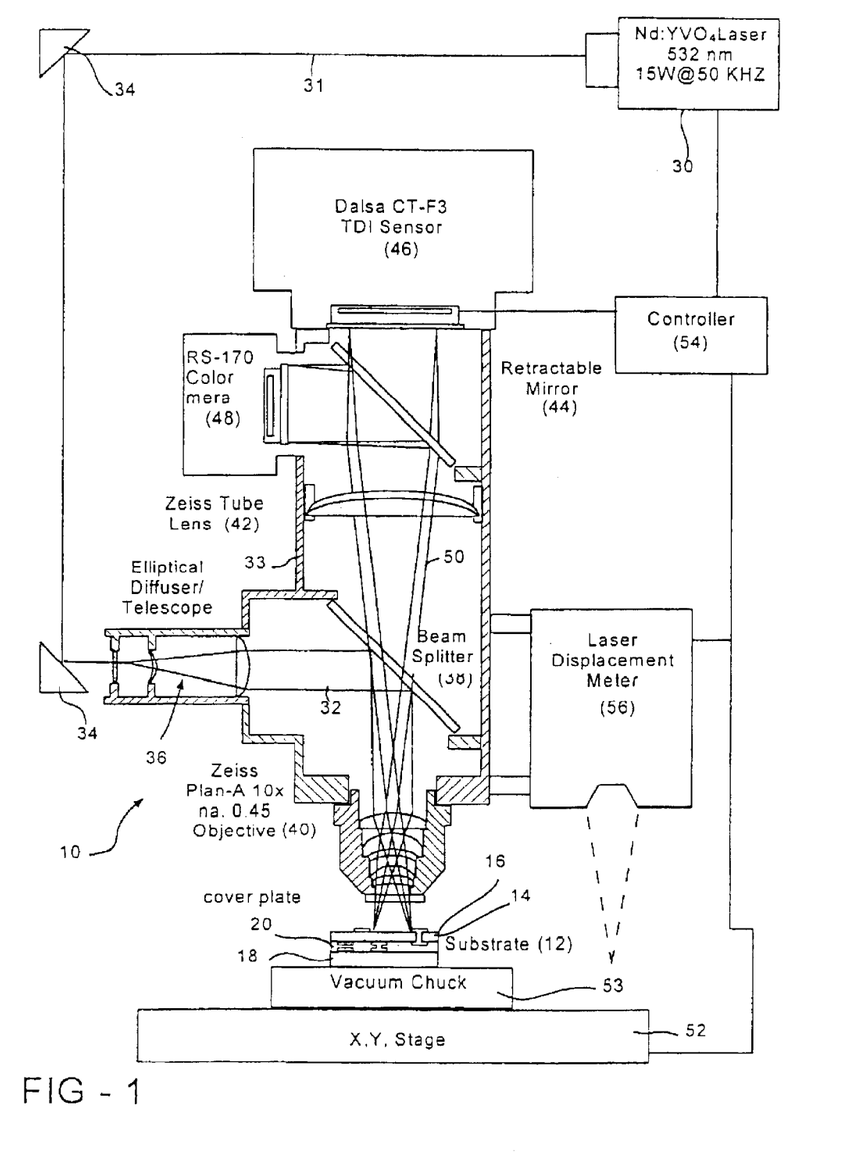
FIG. 1 is a schematic representation of a first preferred embodiment of an imaging system according to the present invention.
Figure 2:
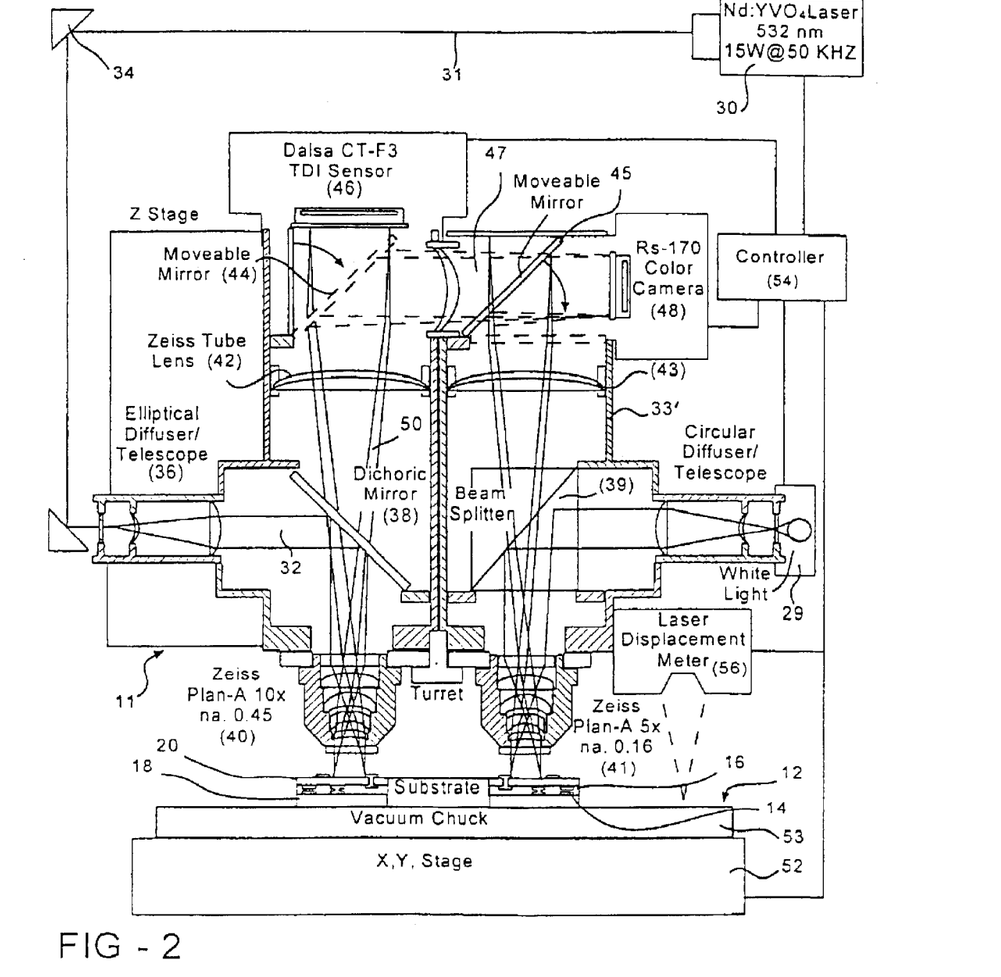
FIG. 2 is a schematic representation of a second preferred embodiment of an imaging system according to the present invention.

With reference to the drawings wherein like elements are numbered alike, and in particular to FIGS. 1 and 2, there are shown a first and a second preferred embodiment of an imaging system generally referenced as 10 and 11 respectively. The first and second preferred embodiments function substantially the same relative to capturing an image of the circuit chip with a TDI sensor. The first and second preferred embodiments differ, however, with regard to the specific manner in which they capture color images of the circuit chip.

Imaging systems 10 and 11 are configured to inspect a circuit board 12. Circuit board 12 includes an inner layer 14, one or more outer layers 16, and may include metallic conductors 18 and/or metallic vias 20. The outer layers are typically composed of an organic substance, for example polyamide while the inner layer may be composed of FR4. Upon illumination from a laser 30 those organic portions of circuit board 12 will illuminate while the inorganic portions will not. This selective fluorescence provides a high contrast image which is well suited for image processing.

For laser 30 to appropriately create fluorescence, it needs to be of a specific wavelength, which for any case is less than the wavelength at which circuit 12 will fluoresce. Here, a typical circuit will emit light at 700 nanometers (nm) and as such laser 30 must emit light at a wavelength less than 700 nm. The preferred laser has a wavelength of 532 nm. Laser 30 is available from Coherent of Santa Clara, Calif. and may be a Coherent Laser Compass Model 501QM-VD, which is a Q-switched green (532 nm) Neodymium-Yttrium Orthvanadate (Nd:YVO$_4$) laser with a peak power of 5 kW @ 15 kHz. Laser 30 emits a series of pulses 31, which are shaped into the form of a pulsed laser stripe 32. As illustrated, laser 30 may be positioned anywhere within or relative to imaging system 10, and its output may be reflected by mirrors 34 along an appropriate path.

Many components of imaging system 10 are contained in a housing 33. These components include beam focusing optics 36, dichroic mirror 38, microscope objective lens 40, tube lens 42 and retractable mirror 44. Attached to housing 33 are a time delay integration (TDI) sensor 46 and a color camera 48. Housing 33 provides an optically shielded environment in which sensor 46 can acquire images of circuit 12.

In particular, laser 30 omits a plurality of timed pulses 31 which are reflected by mirrors 34 into beam shaping optics 36. Preferably, beam shaping optic 36 is an elliptical diffuser/telescope. Suitable elliptical diffuser/telescopes are available from Edmund Industrial Optics of Tonawanda N.Y. These beam shaping optics must be either of air gap construction or must be bonded together with non-organic cement which does not adsorb energy. Beam shaping optics 36 focus Laser pulses 31 into the form of a pulsed laser stripe 32. Thus, when striped laser pulses 32 are ultimately directed to circuit chip 12 the pattern of fluorescence is similarly emitted as a stripe. Because laser 30 is pulsed, rather than continuous, its energy level may be higher than that of a continuous laser. The higher energy results in a higher degree of fluorescence and thus a higher degree of contrast for the TDI sensor when it is imaging the circuit chip.

Pulsed laser stripes 32 are directed towards circuit board 12 from orthogonally above by a dichroic mirror or dichroic filter 38. By directing laser pulses at circuit chip 12 from orthogonally above circuit chip 12, shadows are eliminated. The purpose of dichroic mirror 38 is to reflect laser light, for example, a pulsed laser stripe 32, at one wavelength while allowing reflected light at another wavelength to pass through. In this case, dichroic mirror reflects light having a wavelength of 532 nanometers onto circuit 12 while transmitting the fluorescent light emitted from circuit chip 12, which is centered about 700 nanometers, toward TDI sensor 46. In essence, the filter must reflect nearly 100% of the laser beam and transmit nearly 100% of the reflected fluorescent light. Preferably a red dichroic mirror is used which is also available from Edmund Industrial Optics as Model K52-528. It is understood that other lasers and other dichroic mirrors may be used so long as the laser light is reflected and the light reflected or emitted from circuit chip 12 is passed through.

Striped laser pulses 32 pass through a microscope objective 40 and cause circuit 12 to emit fluorescent light 50 which passes back through microscope objective 40. As is clear from the figures, both striped laser pulses 32 and fluorescent light 50 pass through microscope objective lens 40. As such typical microscope objectives are unacceptable. Typical microscope objectives are unacceptable because they are bonded with organic cements. If laser light of 532 nm were passed through a microscope objective bonded together with organic cement, the organic cement would adsorb energy and increase in temperature. As the microscope objective increased in temperature, it would become unstable and could crack or fail in some other way. Thus, the microscope objective must be bonded with a non-organic cement or be an air gap lens. Such a microscope objective lens is preferably custom ordered from Carl Zeiss, microscopy and imaging systems, of Thornwood N.Y. Microscope objective lens 40 is chosen such that it focuses at the laser stripe on the entire TDI sensor. In this application an air gap or non-fluorescing cement lens similar to the Zeiss A-Plan 10× NA. 0.45 Objective lens with a 0.17 mm cover plate would be preferred.

The preferred TDI sensor is available from Dalsa of Waterloo, Ontario as model CT-F3-2048. This TDI sensor is a bi-directional eight tap TDI sensor which includes 96 columns each having 2048 photo sites. The combination of microscope objective 40 and TDI sensor 46 are such that the laser stripe illuminates the entire TDI sensor 46. As explained above, when clocked, the TDI sensor will transfer all of the charge associated with one column into its adjacent column, enabling the TDI sensor to continue to integrate light into the column.

Circuit chip 12 is mounted on a stage 52 with a vacuum chuck 53. Stage 52 transports circuit chip 12 in the X, Y, and Z axes. Alternately, stage 52 is movable in only the X and Y axis with housing 33 being movable in the Z axis. Preferably, movement along the X, Y, and Z axes is affected by three distinct motors. (Not shown) Linear feed back is provided as to provide accurate movement. Feedback is preferably provided linear encoders. Suitable encoders are available from Acu-Rite as the Acu-Rite ENC150. Three such encoders would be used, one each for the X, Y, and Z axes. These encoders have a resolution of 0.5 microns over their entire range of travel with an absolute accuracy greater than 10 microns per meter.

Stage 52 is configured to move at a defined rate. The defined rate of movement is coordinated with the clock rate of the TDI sensor so that the same portion of circuit chip 12 can be imaged by multiple columns of the TDI sensor. The encoders can be configured to report linear displacement in units of pixels which correspond to the size of the photo sites on TDI sensor 46, which, as explained in greater detail below can be used as feedback to coordinate activation of laser 30 with the clocking of the TDI sensor. In order to maximize through put, stage 34 is substantially in continuous movement.

Figure 3:
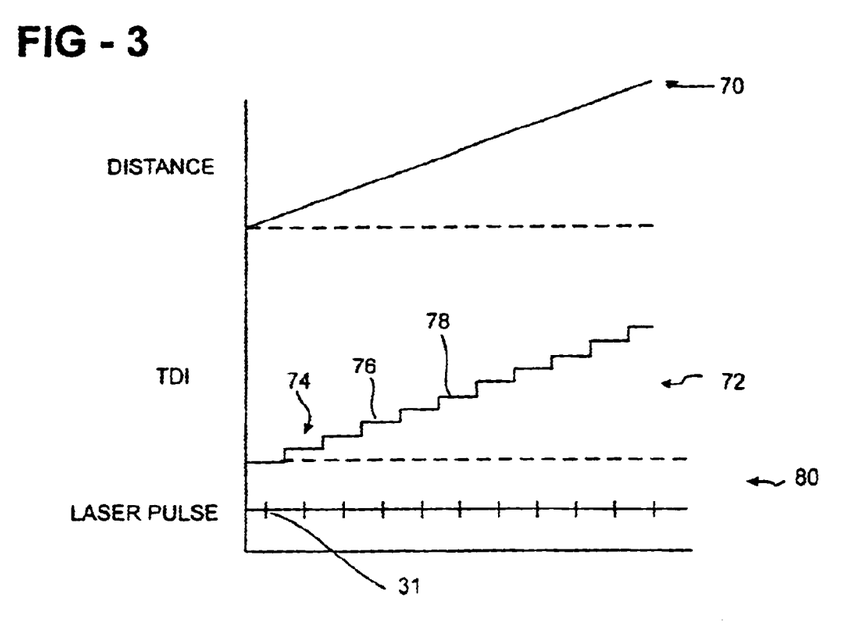
FIG. 3 is a graphical representation illustrating the manner in which a pulsed laser is synchronized with a TDI sensor and movement of a circuit chip to provide an increase in image quality.

With reference to FIG. 3, there is shown a comparative graph illustrating the manner in which laser 30 is coordinated with stage 52 and TDI sensor 46. In particular, the top most graph 70 illustrates the constant movement of the stage 52. For purposes of this example, stage 52 may be presumed to be moving along the X axis. Middle graph 72 illustrates the clocking, or shifting of columns of photo sites on the TDI sensor. Each step 74 illustrates a shift in the charges from one column of photo sites to an adjacent column of photo sites. The horizontal sections 76 of step 64 represents that time during which a charge resides in a column of photo sites while vertical sections 78 of step 78 represents the period during which the charge is shifted from column to column. As can be seen the rate, or slope of graphs 70 and 72 are the same, recognizing that graph 70 is more linear and graph 72 is more step wise. Thus, while the entire TDI sensor is being illuminated by pulsed laser stripe 32, any particular portion of circuit chip is being imaged by a column of photo sites which is moving essentially at the same rate. In this way the image of the same portion of circuit chip 12 is being successfully integrated while the circuit chip being inspected is moving constantly. Lower most graph 80 illustrates the rate at which laser pulses 32 are being fired. As can be seen, laser pulses 31, and thus striped laser pulses 32, occur at the mid period of horizontal section 76 when the charges are residing in any particular column of photo sites. This mid period can also be thought of as one half of a pixel as measured by the linear encoder at the stage. By pulsing laser 30 only when the TDI sensor is charging its photo sites reduces artifacts and decreases smear.

It is understood that while FIG. 3 illustrates that laser pulses fire each time TDI sensor 46 clocks other permutations are possible. For example, laser 30 may fire every other time TDI sensor 46 clocks. This alternate is preferred as it further increases resolution without a significant penalty in image intensity. Integrating TDI sensor 46 less than half the time it clocks tends to decrease image intensity but decreases artifacts. A user may define, how frequently, or infrequently to integrate the charges on the TDI sensor. This will be done based on upon the type of circuit chip being inspected and other user defined criteria.

As stage 52 moves new portions of circuit 12 are imaged by TDI sensor 46 and other parts are clocked out. Typically the process starts when striped laser pulse 32 is just coming into contact with circuit chip 12 and is not complete until pulsed laser stripe 32 is off of circuit chip 12. After the chip is imaged along, for example the X axis, the stage may move in the Y direction and the X axis scanning may start over to complete the imaging process. While this back and forth scanning technique is preferred other options may be available. It is understood that once a complete image is available, it may be analyzed for defects as is customary in the art. The image may be analyzed by a variety of known techniques.

Laser 30 along with the X, Y, and Z axes and TDI sensor are controlled by a Controller 54. Controller 54 is preferably a programmable state machine that executes the state diagram shown in FIG. 4. The controller can be constructed from programmable logic parts such as a Xilinx or Altera or may be constructed using a microprocessor with appropriate inputs/outputs. One such controller is disclosed in co-pending U.S. Provisional Patent Application, Serial No. which is incorporated herein by reference.

Figure 4:
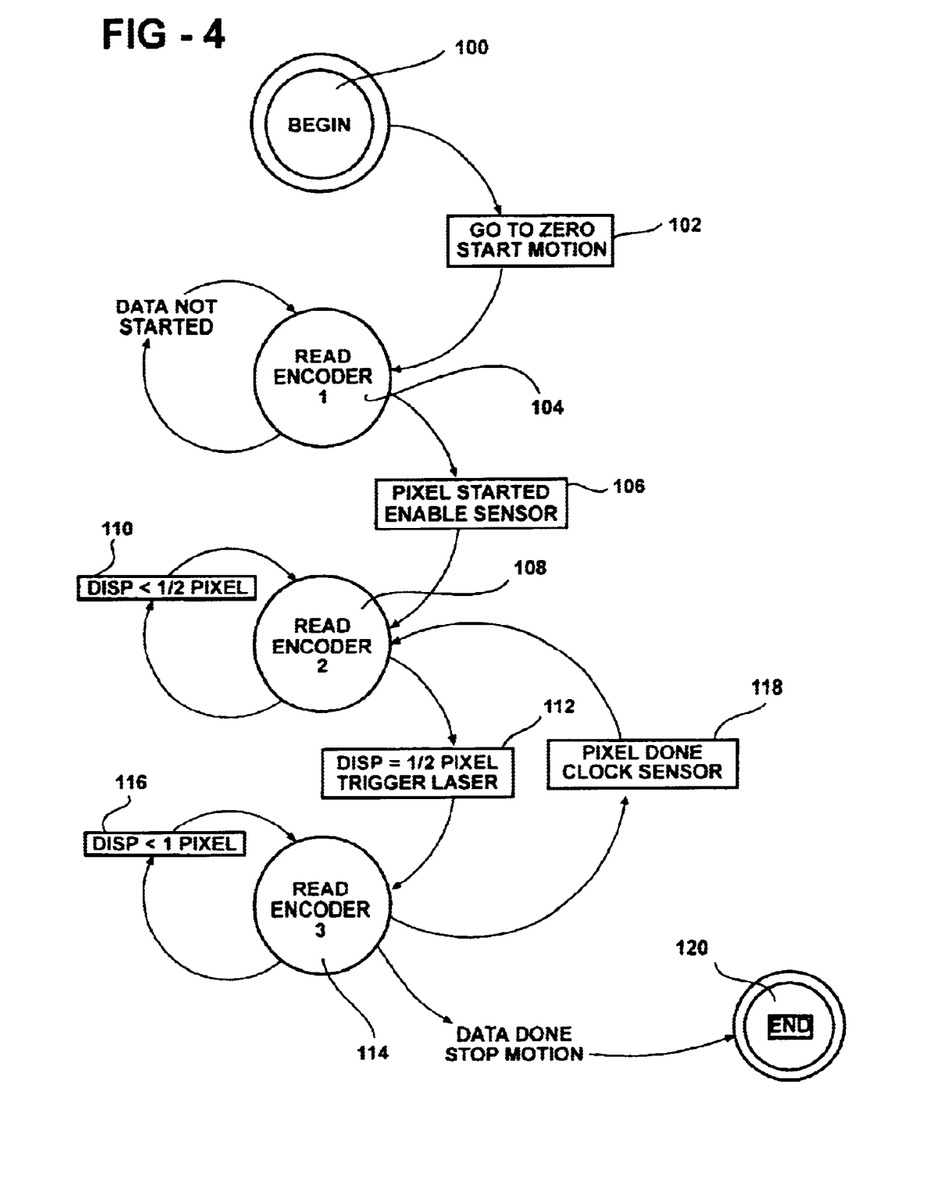
FIG. 4 is a state diagram illustrating the operation of the present invention.

With reference to FIG. 4, the state diagram illustrates the manner is which controller 54 operates. In particular, as referenced at 100 controller 54 initiates operation. As referenced at 102. controller 54 sends a control signal to the X axis drive motor and X-linear encoder to move the stage to a "start" position. The start position is one in which pulsed laser stripe is just off circuit chip 12. Controller 54 then instructs stage 52 to move at a predetermined rate, using the x axis linear encoder for feedback. Controller then transitions to "read encoder 1" as referenced at 104 where the encoder information is input and checked against a preprogrammed value to decide when data acquisition begins, as referenced at 106. In short, TDI sensor begins to gather information in coordination with laser 30 when pulsed laser stripes 32 begin to contact circuit chip 12.

When data acquisition begins, the TDI sensor is activated and the controller transitions to "read encoder 2" referenced at 108. At 108, "read encoder 2," x axis encoder data is read to determine when the displacement of the circuit chip equals the middle of the TDI column, i.e. the central time at which the charges occupy their column of photo sites which is also coined the middle of the pixel. As shown at 110, this is accomplished by measuring displacement as one half of a pixel at 110. When this condition is reached, controller 54 triggers laser 30 as indicated at 112 and controller 54 transitions to "read encoder 3" referenced at 114. At 114, controller 54 continues to check the X axis displacement, shown at 116, to see when the end of the current pixel is reached. After laser 30 has fired, and the X motion is beyond one half a pixel the pixel is indicated as being done and the TDI sensor is clocked at 118. Controller 54 then transitions back to "read encoder 2" as shown at 108. The above described process continues capturing image data until the end of data displacement is reached, at which time X axis motion is stopped. If the entire circuit has not been imaged controller 54 will toggle stage 52 in the Y axis and capture images characteristic of the balance of circuit chip 12. When circuit chip 12 has been captured in its entirety, the process is done at 120.

Again with reference to FIGS. 1 and 2 imaging systems 10 and 11 further include a color camera 48 which is operative to capture a color image of circuit chip 12. FIGS. 1 and 2 illustrate two different preferred configurations for capturing color images of circuit chip. Color images may be captured of the circuit chip so that a user may subjectively evaluate a color image if the system indicates that a defect exists. These subjective evaluations may be cataloged and used later to enhance the image processing algorithms used to inspect the image.

As shown in FIG. 1, there is a color camera 48 and a retractable mirror 44. Color camera 48 and retractable mirror 44 are used to take color photographs of laser stripe 32 as it appears on circuit chip 12 in lieu of having that portion of circuit chip 12 imaged by TDI sensor. Preferably, the movement of mirror 44 is controlled by controller 54. During normal operation mirror 44 is positioned vertically as not to obstruct TDI sensor 46. Mirror 44 is pivoted into place to reflect light onto color camera 48 so that a color picture may be taken. A system user can then manually review the color picture to classify the error.

FIG. 2 illustrates a second preferred configuration for capturing color images of circuit chip. FIG. 2 illustrates an embodiment in which color images may be captured of the laser stripe on the circuit chip, and color images of the circuit chip using white light may be captured. As shown, the second preferred embodiment includes a second housing 33' which is positioned adjacent to housing 33. Second housing 33' is configured to capture color image of circuit chip 12 using white light. Second housing 33' includes a microscope objective 41, a beam splitter 39, a tube lens 43, and a retractable mirror 45. Housing 33 and 33' are connected by path 47 through which color images of laser stripe 32 are captured.

A source of white light 29 is positioned to emit white light through a housing 33'. The white light is shaped by a circular diffuser/telescope and directed onto circuit chip 12 by a beam splitter 39. Appropriate diffuser/telescopes and beam splitters are available from Edmund Industrial Optics. The reflected white light passes through beam splitter 39 and illuminates circuit chip 12. The white light is focused on circuit chip 12 by microscope objective 41. Microscope objective 41 is a standard, off the shelf, microscope and is not subject to the same restrictions as compared to microscope objective 40. Preferably, microscope objective 41 is a Zeiss Plan-A 5× NA. 0.16. The light reflected from circuit chip 12 passes back through microscope objective 41, through beam splitter 39, through tube lens 43 and is reflected onto camera 48 by a retractable mirror 45.

As shown in FIG. 2 the second alternate embodiment utilizes a single color camera identical to that of the first preferred embodiment. In this case, and as appreciated from FIG. 2, mirrors 44 and 45 may be selectively pivoted such that a color photo of pulsed laser stripe 32 may be captured (mirror 44 in its angled position, mirror 45 in its flat position); a color photo using white light may be captured (mirror 45 in its angled position), or; imaging system can use TDI sensor to capture an image of circuit chip 12 (mirror 44 in its vertical position, mirror 45 in its angled position). Like the first preferred embodiment, mirrors 44 and 45 are controlled with controller 54, although they may be controlled in response to a user selection relative to capturing a color image of laser stripe 32 or capturing a color image of circuit chip 12 using white light.

Imaging system 10 may also include a laser displacement meter 56 which is coupled to controller 54. Laser displacement meter 56 provides constant and accurate feedback as to the distance circuit chip 12 is away from microscope objective 40. Because microscope objective 40 has a very shallow depth of field, it may need to be adjusted depending on the height of circuit chip 12. By constantly tracking the Z axis displacement, controller 54 can adjust stage 52 in the Z axis to keep circuit chip 12 constantly in focus.

While this invention has been described in terms of a circuit chip which fluoresces, it is understood that other types of chips may also be inspected using the teachings of the present invention. It should be understood that the present invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. An apparatus for inspecting a circuit chip where the circuit chip is on a movable stage, the stage moving substantially continuously along an axis at a defined rate the apparatus comprising;

a pulsed laser including a lens system operative to emit a stripe of laser pulses at controlled intervals, the pulses being directed toward the circuit chip as to illuminate the circuit chip;

a time delay integration sensor for capturing an image of the circuit chip, the sensor defined by an array of photo sites, having at least one row of photo sites and a plurality of columns of photo sites, each photo site being chargeable, the sensor operative to transfer a charge from column to column at a defined rate, the sensor and movable stage being coordinated such that the charges are being clocked from column to column at the same rate at which the stage is moving;

a controller connected to the pulsed laser and configured to activate the laser in synchronization with the rate at which the sensor transfers charges from column to column such that the laser is activated when the charge resides in a column of photo sites and the laser is deactivated when the charge is being transferred from column to column.

2. An apparatus as in claim 1 wherein the laser pulses cause the circuit chip to fluoresce.

3. An apparatus as in claim 2 wherein the laser pulses are directed toward the circuit chip with a dichroic mirror and the time delay integration sensor is positioned orthogonally above the circuit chip.

4. An apparatus as in claim 3 wherein the laser pulses have a wavelength of less than 700 nanometers.

5. An apparatus as in claim 3 wherein the dichroic mirror directs the laser pulses toward the circuit chip from orthogonally above.

6. A apparatus as in claim 3 wherein the laser pulses along with the fluorescent light from the circuit chip pass through a microscope objective lens.

7. An apparatus as in claim 1 wherein the controller is further connected to the movable stage and to the time delay integration sensor; the controller operative in determining whether the stage is moving at the same rate as the rate at which the charges are being shifted from column to column in the time delay integration sensor and the controller being operative to adjust the rate at which the stage is moving.

8. An apparatus as in claim 7 wherein the controller measures the movement of the stage in units of pixels which correspond to the size of the photo sites on the time delay integration sensor.

9. An apparatus as in claim 8 wherein the controller is operation to activate the laser when it determines that the stage has moved a half of a pixel.

10. An apparatus as in claim 7 further comprising means for monitoring a Z axis displacement of the circuit chip, and means for adjusting the Z axis displacement in response to the means for monitoring.

11. An apparatus as in clam 2 further comprising a color camera configured to selectively capture images of the circuit chip.

12. An apparatus as in claim 11 further comprising a source of white light configured to illuminate the circuit chip.

13. A method for inspecting a circuit chip where the circuit chip is on a movable stage, the stage moving substantially continuously along an axis at a defined rate, the method comprising imaging the circuit chip with a time delay integration sensor, the sensor defined by an array of photo sites, having at least one row of photo sites and a plurality of columns of photo sites, each photo site being chargeable, the sensor operative to transfer a charge from column to column at a predefined rate, the time delay integration sensor and movable stage being coordinated such that the charges are being clocked from column to column at the same rate at which the stage is moving;

pulsing a stripe of laser pulses toward the circuit chip as to illuminate the circuit chip where the laser pulses are in synchronization with the rate at which the sensor transfers charges from column to column such that the laser is activated when the charge resides in a column and the laser is deactivated when the charge is being transferred from column to column.

14. A method as in claim 13 wherein the laser pulses cause the circuit chip to fluoresce.

15. A method as in claim 14 wherein the laser pulses are reflected toward the circuit chip with a dichroic mirror and the time delay integration sensor is positioned orthogonally above the circuit chip.

16. A method as in claim 13 wherein a controller is operative in pulsing the laser in synchronization with the rate at which the sensor transfers charges.

17. A method as in claim 16 wherein the controller is connected to the movable stage and to the time delay integration sensor; the controller operative in determining whether the stage is moving at the same rate as the rate at which the charges are being shifted from column to column in the time delay integration sensor and the controller being operative to adjust the rate at which the stage is moving.

18. A method as in claim 17 wherein the controller measures the movement of the stage in units of pixels which correspond to the size of the photo sites on the time delay integration sensor.

19. A method as in claim 18 wherein the controller is operative to activate the laser when it determines that the stage has moved a half of a pixel.

20. A method as in claim 13 further comprising capturing a color image of the circuit chip.

21. A method as in claim 20 further comprising illuminating the circuit chip with white light.

* * * * *